United States Patent [19]
Persson et al.

[11] Patent Number: 5,549,120
[45] Date of Patent: Aug. 27, 1996

[54] APPARATUS FOR APPLYING AN ELASTIC PROTECTIVE SHEATH ON AN ELONGATE BODILY MEMBRANE, AND PROTECTIVE AID ARTICLE HAVING SUCH AN APPARATUS

[76] Inventors: Lars Persson, Myra 2256, Järvsö, S-820 40; Kjell Karlsson, Läsarvägen 13, Ljusne, S-820 20; Lise-Lotte Lundgren, Mjölnäsvägen 5, Norrala, S-826 62, all of Sweden

[21] Appl. No.: 331,486

[22] Filed: Nov. 7, 1994

[30] Foreign Application Priority Data

May 7, 1992 [SE] Sweden ................... 9201438

[51] Int. Cl.$^6$ .................. A61F 6/02; A61F 6/04
[52] U.S. Cl. .................. 128/842; 128/844; 128/918
[58] Field of Search ................. 128/842, 844, 128/918; 604/347–353

[56] References Cited

U.S. PATENT DOCUMENTS

| | | |
|---|---|---|
| 2,567,926 | 9/1951 | Dunkelberger . |
| 2,591,783 | 4/1952 | Craddock .................. 604/353 |
| 2,904,041 | 9/1959 | Brown ..................... 128/844 |
| 3,203,420 | 8/1965 | Lockhart .................. 604/353 |
| 3,999,550 | 12/1976 | Martin .................... 604/353 |
| 4,588,397 | 5/1986 | Giacalone ................. 604/351 |
| 4,664,104 | 5/1987 | Jaicks .................... 604/353 |
| 4,875,491 | 10/1989 | Parrone . |
| 5,163,449 | 11/1992 | van der Valk ............. 128/844 |

*Primary Examiner*—Michael A. Brown

[57] ABSTRACT

A device for applying a condom on the penis, having an annular or arcuate frame that is of a greater width than the penis and having on the outside, a seating against which an annular rolled-up portion of the condom wall can be applied and which is defined by peripheral beads elevated over the seating. The annular frame has a slit, separating two end portions are movable transversely on the plane of the annular frame to facilitate the removal of the frame.

7 Claims, 3 Drawing Sheets

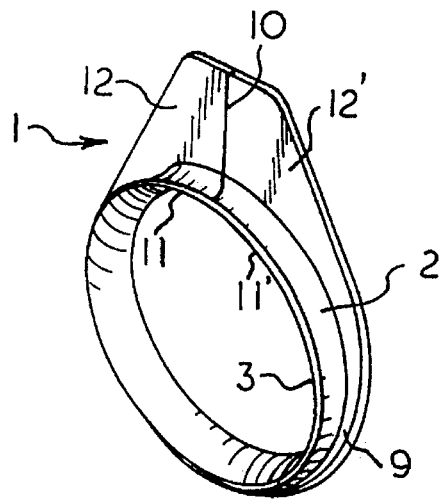 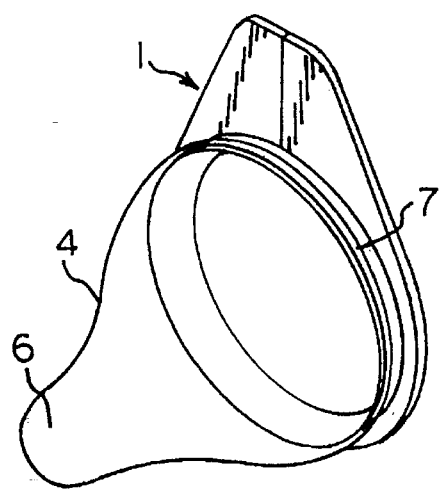
FIG. 1     FIG. 2
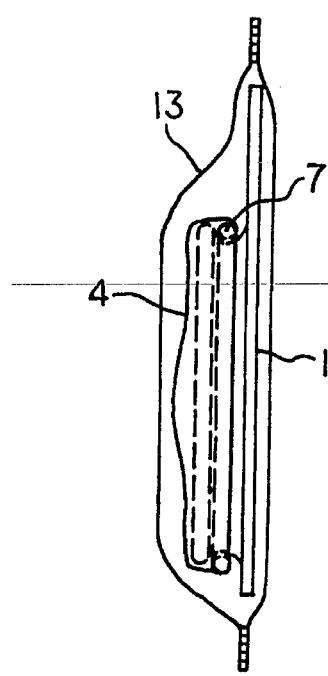 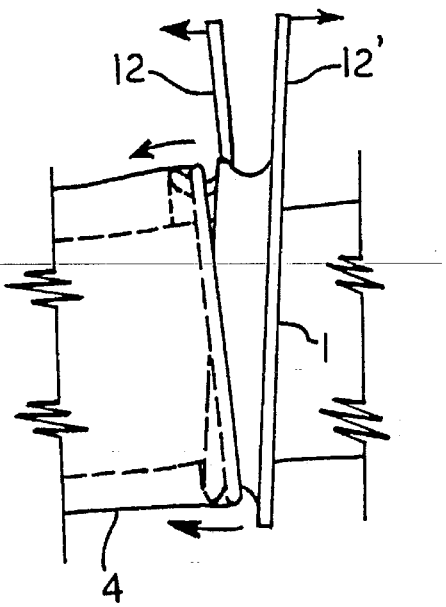
FIG. 3     FIG. 5

APPARATUS FOR APPLYING AN ELASTIC PROTECTIVE SHEATH ON AN ELONGATE BODILY MEMBRANE, AND PROTECTIVE AID ARTICLE HAVING SUCH AN APPARATUS

FIELD OF THE INVENTION

In a first aspect, the invention relates to an apparatus for applying an elastic protective sheath, e.g. a condom, on an elongate bodily member, said sheath consisting of a tubular wall which is open at one end and which is closed or closable by a bottom at the other end, the tubular wall of said sheath, in an initial position of the sheath before being applied on said bodily member, being rolled into an annular elastic configuration, said means consisting of an annular or arcuate frame which, at least when the sheath is to be applied, has a greater width than said bodily member and which, on the outside, has a seating against which the annular, rolled wall portion of the bag-like sheath can be applied and which is defined by two spaced-apart, peripheral collars or beads raised from said seating and serving to retain the rolled tubular wall portion on the seating while at the same time the tubular wall proper is unrolled from said rolled portion when said frame is placed on and moved axially along said bodily member, one of said collars or beads being higher than the other.

DESCRIPTION OF THE PRIOR ART

The use of conventional condoms, which has become increasingly widespread with the advent of HIV, is inconvenient in many ways. It is difficult and takes time to apply the condom on the penis, requiring the use of both hands. Further, the condom is easily turned inside out, especially when used in the dark. When touching the condom, the fingers are smeared with glidant and come to smell of glidant as well as rubber. In addition, the condom is easily torn by the nails, thereby ceasing to prevent conception as well as infection. Condoms being applied in a state of excitement, the procedure is felt to be an annoyance, often by both parties. As a result, the male may even lose his erection, and no intercourse can take place.

The difficulties experienced when applying a urisheath on a patient's penis are roughly the same. In this case, however, the penis is usually limp, which means that the assistant nurse has to use one hand for keeping the penis extended, leaving but one hand for unrolling the urisheath. It is easily understood that this procedure may be embarrassing, leading to tense and strained relations between the assistant nurse and the patient.

In order to remedy the inconveniences related above, special application means have been developed, serving to facilitate the application of the protective sheath or condom on the penis. Thus, WO92/06657 teaches a means of the type mentioned by way of introduction. In this prior-art means, however, the annular frame is whole or continuous along the periphery, necessitating the provision of an ejector pin for separating the frame from the condom, once the latter has been applied. In practice, such an ejector mechanism is highly disadvantageous, not only because it considerably enhances the costs of producing the application means, but also because of the manifest risk of it being inadvertently activated, e.g. by the exertion of a light pressure when stored in a pocket.

FURTHER ELUCIDATION OF THE PRIOR ART

U.S. Pat. No. 4,875,491 teaches four different embodiments of an application means. It is true that one of these embodiments, illustrated in FIGS. 4 and 5, has a separating slit. However, the U.S. application means does not comprise an annular frame with two spaced-apart peripheral annular beads defining a condom-retaining seating. Thus, the frame of the U.S. application means is a flat disc to which the condom is fixed by an adhesive layer, the condom being folded in accordion-like fashion, and not rolled up. The purpose of the slit is to enable the annular frame to be removed from the penis by being broken apart, rather than moved back along the penis. Although the adhesive layer is then disintegrated, this of course implies that the condom is fully stretched. The present invention, on the other hand, makes it possible to separate the application means from the condom regardless of how stretched the condom is, i.e. regardless of the length of the penis. Another important difference is that the U.S. application means lacks gripping flanges of the type that distinguishes the inventive means, and it should here be emphasized that the components 76, 84, 136 and 144 in the U.S. specification constitute gripping flaps of elastic package coverings, and not gripping flanges forming part of the annular frame proper.

SUMMARY OF THE INVENTION

This invention aims as remedying the above inconveniences of the prior-art application means and providing a means making it possible to unroll and extend the initially rolled-up condom or sheath, which then can be rapidly and expediently removed from the application means without the use of any complicated and expensive ejector mechanism that might be inadvertently activated. According to the invention, this aim is achieved by an apparatus for applying an elastic protective sheath on an elongate bodily member, said sheath having a tubular wall which is open at one end and which is closed or closable at the other end, and in an initial position the tubular wall of the sheath is rolled into an annular elastic configuration, said apparatus comprising:

a substantially annular resilient frame adapted to accommodate said bodily member, two spaced apart peripheral beads provided on an outside surface of the frame, one of the beads being higher than the other which together define an annular groove on the outside surface of the frame providing a seating for receiving the annular rolled tubular wall portion of the sheath, a removal means for removing the sheath from the frame once the sheath has been applied to the bodily member including a slit or opening extending from the outside surface to an inside surface separating two end portions of the frame, and enlarged flange members on either end portion of the frame formed integrally on the higher bead to serve as gripping means, each flange member, due to the inherent flexibility of the annular frame, being movable in relation to the other from a first position substantially coplanar with the frame to a second position spaced apart transversely of the plane of the annular frame, whereby the peripheral beads are separated displacing the sheath from the seating.

In a second aspect, the invention relates to a protective aid article comprising in combination: an elastic protective sheath having a tubular wall which is open at one end and which is closed or closable at the other end, the tubular wall of said sheath being, in an initial position of the sheath, rolled into an annular elastic configuration, and an apparatus for applying the sheath to an elongate bodily member including:

a substantially annular resilient frame which, is adapted to accommodate said bodily member, two spaced apart peripheral beads provided on an outside surface of the frame, one of the beads being higher than the other which together define an annular groove on the outside surface of the frame providing a seating for receiving the annular rolled tubular wall portion of the sheath, a removal means for removing the sheath from the frame once the sheath has been applied to the bodily member including a slit or opening extending from the outside surface to an inside surface separating two end portions of the frame, and enlarged flange members on either end portion of the frame formed integrally on the higher bead to serve as gripping means, each flange member, due to the inherent flexibility of the annular frame, being movable in relation to the other from a first position substantially coplanar with the frame to a second position spaced apart transversely of the plane of the annular frame, whereby the peripheral beads are separated displacing the sheath from the seating, and wherein said protective elastic sheath is mounted on the application apparatus so that the tubular wall of the sheath can be tangentially unrolled from the annular configuration in the peripheral area thereof located at a distance from the seating of the apparatus, the closed end of the sheath passing over the lower bead of the annular frame, and the combination is enclosed in a package readily configured for use. In this preferred embodiment, both the condom or urisheath and the application means are disposable.

BRIEF DESCRIPTION OF THE DRAWINGS

In the drawings,

FIG. 1 is a perspective view of a preferred embodiment of the application means according to the invention;

FIG. 2 is a similar perspective view of a condom mounted on the application means;

FIG. 3 is a cross-section of a protective aid article according to the invention;

FIG. 5 is a side view illustrating how the inventive means is removed from the applied condom.

DETAILED DESCRIPTION OF A PREFERRED EMBODIMENT

The application means shown in FIG. 1 consists of an annular or arcuate frame 1 which, on the outside, has a circumferential seating 2 (see also FIG. 6) which on both sides is defined by peripheral collars or beads 3, 9 raised from the seating.

Figure 4:
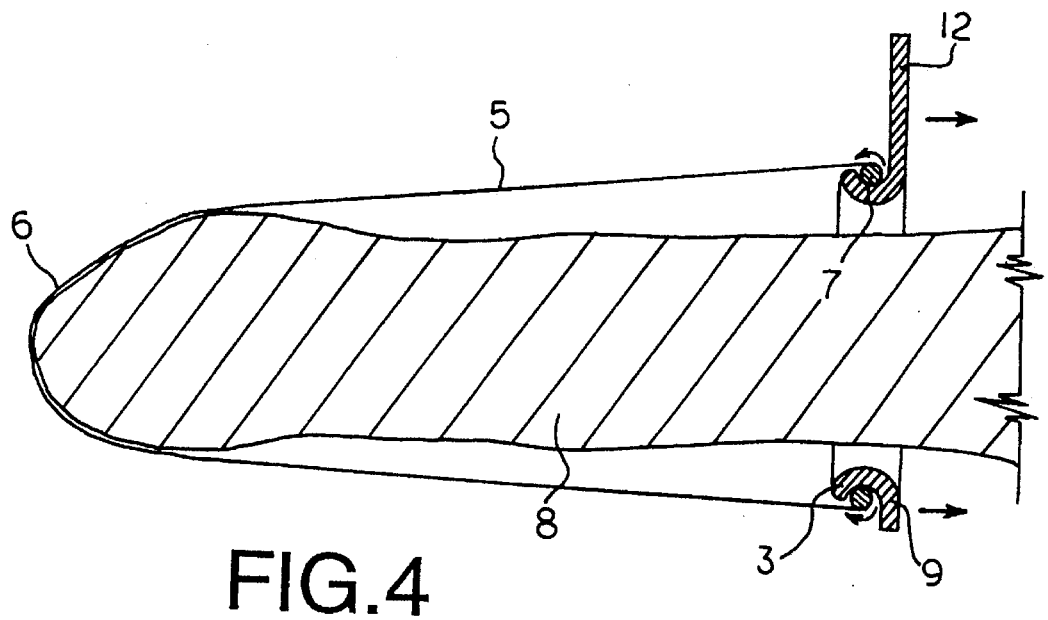
FIG. 4 is a partly sectional side view illustrating the function of the application means when a condom is being applied on the penis.

In conventional manner, the condom shown in FIGS. 2–4 and generally designated 4 is in the form of a bag having a tubular wall 5 which is open at one end and which is closed by a bottom 6 at the other end. In an initial position, the tubular wall portion 5 is rolled into an annular elastic configuration or roll 7 which can be applied on the seating 2, in which case the bead 3, which is raised or projecting from the seating, retains the rolled portion 7 on the seating, while at the same time the tubular wall proper 5 is unwound from the rolled portion when the annular or arcuate frame 1 is placed on, and moved axially along, the penis designated 8 in FIG. 4.

Figure 6:
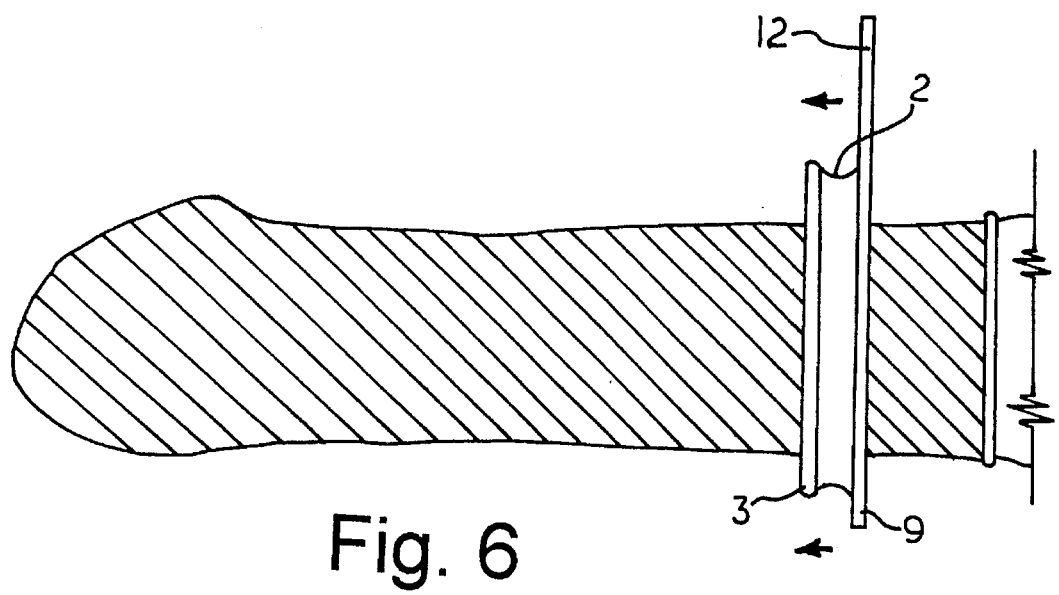
FIG. 6 is a side view illustrating the removal of the inventive means from the penis.
Figure 7:
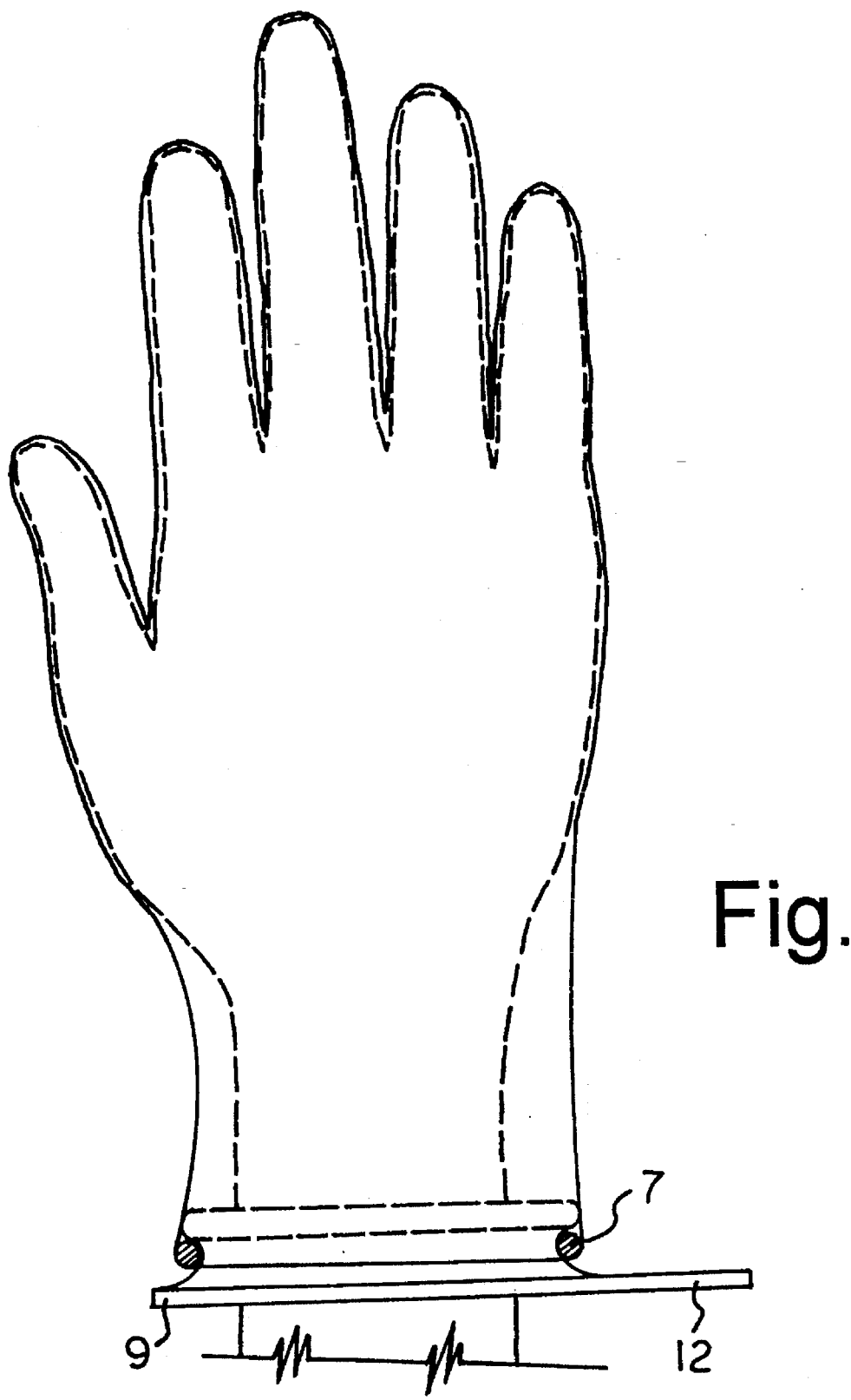
FIG. 7 is a part sectional view illustrating the function of the application means for applying a rubber glove to a hand.

Advantageously, the other collar or bead 9, located on the side of the seating 2 opposite to the bead 3, is higher than the bead 3, as can be seen in FIG. 6. Because the seating 2 is thus defined by two beads, one on each side, the seating becomes the bottom of a circumferential groove in the frame.

The annular frame 1 has a slit or opening 10 separating two end portions 11, 11' which, owing to the inherent elasticity of the annular frame, are movable in relation to one another transversely of the plane of the annular frame, as clearly shown in FIG. 5. This arrangement considerably facilitates the removal of the annular frame once the condom has been applied on the penis.

As appears from the drawings, one of the two beads 3, 9, more precisely the higher one 9, is partially enlarged by two flanges 12, 12' which project from the remainder of the bead and are located one on each side of the separating slit 10 and which are intended to serve as gripping means for the fingers. The two flanges are easily kept together by the forefinger and the thumb when the condom is being applied, while at the same time the annular rolled portion 7 of the condom is securely retained in the groove between the beads 3, 9. Then, the two flanges are easily displaced axially in relation to one another by the fingers of one hand, as illustrated in FIG. 5. The open end of the condom is thus pulled off the bead 3, so that the annular frame 1 is clear of the condom.

The application means described can be manufactured and sold as a separate, conveniently re-usable article on which conventionally packed condoms are applied by hand when to be used. However, the application means is preferably disposable. More precisely, a condom is then applied to the means and enclosed together therewith in a package 13, as illustrated in FIG. 3, as early as the factory. In practice, the package 13 can be a hermetically sealed flexible plastic cover of essentially the same type as is conventionally used for condoms. In the embodiment shown in FIG. 3, the condom 4 and the application means 1 together form a disposable protective aid article, the condom being readily unrolled from the application means once the package 13 has been removed.

Conveniently, the application means is made of rigid plastic, but other materials, such as metal, may also be used. In the shown embodiment using a separating slit, it is, however, of importance that the chosen material has at least a certain inherent elasticity, so that the two free end portions of the frame can be separated axially, as described above.

When mounting the condom on the application means, e.g. as shown in FIG. 3, it is important that the condom can be tangentially unwound from the annular rolled portion 7 in the peripheral area at a distance from the seating 2, so that the bottom 6 of the condom and the tubular wall portion 5 pass over the first, comparatively low bead 3 of the annular frame. Owing to the tubular wall of the condom passing out from the external peripheral area of the annular roll 7 (as opposed to being unrolled from the inside of the annular roll 7), the tubular wall will be unwound from the roll without being squeezed between the roll and the frame, which makes it a particularly smooth and easy procedure.

In use, once the package 13 has been removed, the flanges 12, 12' are gripped by the fingers of one hand, and the annular frame is passed on to the free end of the penis. Then, the annular frame is moved axially along the penis, and the tubular wall portion 5 is unwound from the annular roll 7 a distance corresponding to the length of the penis. Then, the application means is released from what remains of the annular rolled portion 7 by the flanges 12, 12' being separated axially, as illustrated in FIG. 5, whereupon the application means is returned along the penis, as illustrated in FIG. 6. In actual practice, the entire procedure can be reliably performed in a few seconds without the user having to touch the condom with his hands.

CONCEIVABLE MODIFICATIONS OF THE INVENTION

It goes without saying that the invention is not restricted to the embodiment described above and shown in the drawings. Thus, the invention can be applied not only to condoms, but also to other elastic protective sheaths, such as urisheaths. Arguably, an interesting area of application concerns elastic protective gloves of the type that, apart from a finger portion, has a sleeve portion and is used by surgeons and other medical staff, among others. Within the scope of the invention, it is thus conceivable to design an annular frame on which the rolled-up sleeve portion of the glove can be applied, while at the same time the finger portion of the glove projects from the frame. Then, the user can introduce his fingers into the finger portion of the glove, to subsequently unroll the sleeve portion rapidly and comfortably by pushing the arm forwards through the annular frame. This dispenses with the need of assisting personnel, e.g. when disinfected gloves are to be put on.

Although the shown preferred embodiment of the annular frame forming the application means has an extremely narrow slit between the end portions, the frame may also have a fairly broad opening between free end portions. If so, the frame becomes rather arched or U-shaped. It should further be pointed out that the seating 2 need not be continuous or whole along the periphery of the annular frame. Thus, the seating may be provided with a number of spaced-apart holes or openings, e.g. in order to save material. Also the design of the two beads 3, 9 defining the seating may vary. Thus, the individual bead need not be continuous along the periphery of the entire annular frame, a perfectly functional bead being formed by a number of spaced-apart studs or projections which together retain the annular rolled portion of the condom or sheath in the seating or the groove when the condom or sheath is to be unrolled. Also, it should here be pointed out that the annular frame may be composed of two parts instead of one, as shown in the drawings. Thus, the frame may be a clip which is made of up two parts and which initially is fairly small but is widened after the rolled-up condom has been applied, so that the seating is pressed against the elastic rolled-up wall portion of the condom. The idea of giving the frame an enlargeable width or diameter is applicable also to annular frames made in one piece. Thus, the annular frame can, when packed together with the condom, have its free end portions bent inwards beyond one another and locked in this position by suitable locking means which are removed once the package has been opened, the frame end portions exerting a spring action and being applied against the rolled-up annular portion of the condom or urisheath. This embodiment has the advantage that the elasticity of the condom is not impaired when the condom is stored for a long time.

We claim:

1. An apparatus for applying an elastic protective sheath on an elongate bodily member, said sheath having a tubular wall which is open at one end and which is closed or closable at the other end, and in an initial position the tubular wall of the sheath is rolled into an annular elastic configuration, said apparatus comprising:

a substantially annular resilient frame adapted to accommodate said bodily member, two spaced apart peripheral beads provided on an outside surface of the frame, one of the beads being higher than the other which together define an annular groove on the outside surface of the frame providing a seating for receiving the annular rolled tubular wall portion of the sheath, a removal means for removing the sheath from the frame once the sheath has been applied to the bodily member including a slit or opening extending from the outside surface to an inside surface separating two end portions of the frame, and enlarged flange members on either end portion of the frame formed integrally on the higher bead to serve as gripping means, each flange member, due to the inherent flexibility of the annular frame, being movable in relation to the other from a first position substantially coplanar with the annular frame to a second position spaced apart transversely of the plane of the annular frame, whereby the peripheral beads are separated, displacing the sheath from the seating.

2. An apparatus for applying an elastic protective sheath on an elongate bodily member as claimed in claim 1 wherein the elastic protective sheath is a condom.

3. An apparatus for applying an elastic protective sheath on an elongate bodily member as claimed in claim 1 wherein the elastic protective sheath is a urisheath.

4. An apparatus for applying an elastic protective sheath on an elongate bodily member as claimed in claim 1 wherein the elastic protective sheath is a disposable glove.

5. A protective aid article comprising in combination: an elastic protective sheath having a tubular wall which is open at one end and which is closed or closable at the other end, the tubular wall of said sheath being, in an initial position of the sheath, rolled into an annular elastic configuration, and an apparatus for applying the sheath to an elongate bodily member including:

a substantially annular resilient frame is adapted to accommodate said bodily member, two spaced apart peripheral beads provided on an outside surface of the frame, one of the beads being higher than the other which together define an annular groove on the outside surface of the frame providing a seating for receiving the annular rolled tubular wall portion of the sheath, a removal means for removing the sheath from the frame once the sheath has been applied to the bodily member including a slit or opening extending from the outside surface to an inside surface separating two end portions of the frame, and enlarged flange members on either end portion of the frame formed integrally on the higher bead to serve as gripping means, each flange member, due to the inherent flexibility of the annular frame, being movable in relation to the other from a first position substantially coplanar with the annular frame to a second position spaced apart transversely of the plane of the annular frame, whereby the peripheral beads are separated, displacing the sheath from the seating, and wherein said protective elastic sheath is mounted on the application apparatus, and the combination is enclosed in a package readily configured for use.

6. A protective aid article as claimed in claim 5 wherein said protective elastic sheath is mounted on the apparatus for applying the sheath so that the tubular wall of the sheath can be tangentially unrolled from the annular configuration in the peripheral area thereof located at a distance from the seating of the apparatus, the closed end of the sheath passing over the lower bead of the annular frame.

7. An apparatus for applying an elastic protective sheath on an elongate bodily member, the sheath having a tubular wall which is open at one end and which is closed or closable at the other end, and in an initial position the tubular wall of the sheath is rolled into an annular elastic configuration, said apparatus comprising:

a one piece substantially annular resilient frame having two separable end portions in facing relation, said frame adapted to accommodate the bodily member, two peripheral beads on an outside surface of the frame in spaced apart parallel planes, one of the beads being higher than the other which together define an annular groove on the outside surface of the frame providing a seating for receiving the annular rolled tubular wall portion of the sheath, two enlarged flange members on either separable end portion of the frame formed integrally on the higher bead to serve as gripping means for separating the end portions transversely from the parallel planes of the beads, whereby when the two end portions are separated, the annular rolled tubular wall portion of the sheath is displaced from the seating.

* * * * *